(12) United States Patent
Corcoran et al.

(10) Patent No.: US 7,582,104 B2
(45) Date of Patent: Sep. 1, 2009

(54) DAISY DESIGN FOR OCCLUSION DEVICE

(75) Inventors: Michael P. Corcoran, Woodbury, MN (US); Joseph A. Marino, Apple Valley, MN (US)

(73) Assignee: Cardia, Inc., Burnsville, MN (US)

( * ) Notice: Subject to any disclaimer, the term of this patent is extended or adjusted under 35 U.S.C. 154(b) by 222 days.

(21) Appl. No.: 11/007,542

(22) Filed: Dec. 8, 2004

(65) Prior Publication Data

US 2006/0122646 A1    Jun. 8, 2006

(51) Int. Cl.
*A61B 17/08* (2006.01)
(52) U.S. Cl. ........................ 606/215; 606/151
(58) Field of Classification Search .................. 606/213, 606/232, 151, 215–217; 623/1.13, 1.22
See application file for complete search history.

(56) References Cited

U.S. PATENT DOCUMENTS

| | | | |
|---|---|---|---|
| 3,874,388 A | 4/1975 | King et al. | |
| 4,007,743 A | 2/1977 | Blake | |
| 4,917,089 A | 4/1990 | Sideris | |
| 5,108,420 A | 4/1992 | Marks | |
| 5,171,259 A | 12/1992 | Inoue | |
| 5,284,488 A | 2/1994 | Sideris | |
| 5,334,137 A | 8/1994 | Freeman | |
| 5,334,217 A | 8/1994 | Das | |
| 5,382,260 A | 1/1995 | Dormandy, Jr. et al. | |
| 5,397,331 A | 3/1995 | Himpens et al. | |
| 5,425,744 A | 6/1995 | Fagain et al. | |
| 5,433,727 A | 7/1995 | Sideris | |
| 5,451,235 A | 9/1995 | Lock et al. | |
| 5,634,936 A | 6/1997 | Linden et al. | |
| 5,649,950 A | 7/1997 | Bourne et al. | |
| 5,702,421 A | 12/1997 | Schneidt | |
| 5,709,707 A | 1/1998 | Lock et al. | |
| 5,725,552 A | 3/1998 | Kotula et al. | |
| 5,741,297 A | 4/1998 | Simon | |
| 5,904,703 A | 5/1999 | Gilson | |
| 6,024,756 A | 2/2000 | Huebsch et al. | |
| 6,171,329 B1 * | 1/2001 | Shaw et al. .................. | 606/213 |
| 6,174,322 B1 * | 1/2001 | Schneidt ...................... | 606/213 |
| 6,206,907 B1 | 3/2001 | Marino et al. | |
| 6,355,052 B1 * | 3/2002 | Neuss et al. ................. | 606/213 |
| 6,379,368 B1 | 4/2002 | Corcoran et al. | |

(Continued)

FOREIGN PATENT DOCUMENTS

DE           233 303 A1      2/1986

(Continued)

*Primary Examiner*—Todd E Manahan
*Assistant Examiner*—Katherine M Dowe
(74) *Attorney, Agent, or Firm*—Kinney & Lange, P.A.

(57) ABSTRACT

The present invention is an occlusion device having a collapsible frame which allows the occlusion device to be more easily centered in a defect and retrieved in situ. The occlusion device comprises a first post configured to be located on a first side of a defect, a second post configured to be located on a second side of the defect, and a fixation device connected to the first and second posts. The fixation device is used to hold the occlusion device in place across a defect, and comprises several segments. The segments are shaped so that each segment comprises a loop, causing the fixation device to resemble a "daisy design."

26 Claims, 9 Drawing Sheets

U.S. PATENT DOCUMENTS

| | | | |
|---|---|---|---|
| 6,511,496 B1 * | 1/2003 | Huter et al. | 606/200 |
| 6,712,836 B1 * | 3/2004 | Berg et al. | 606/213 |
| 7,097,653 B2 * | 8/2006 | Freudenthal et al. | 606/213 |
| 2004/0093022 A9 * | 5/2004 | Kurz et al. | 606/213 |

FOREIGN PATENT DOCUMENTS

| | | |
|---|---|---|
| DE | 4222291 | 1/1994 |
| EP | 0 362 113 A1 | 4/1990 |
| EP | 0 541 063 A2 | 5/1993 |
| EP | 0 541 063 A3 | 5/1993 |
| EP | 0 541 063 B1 | 9/1998 |
| GB | 2 269 321 A | 2/1994 |
| GB | 2269321 A * | 2/1994 |

* cited by examiner

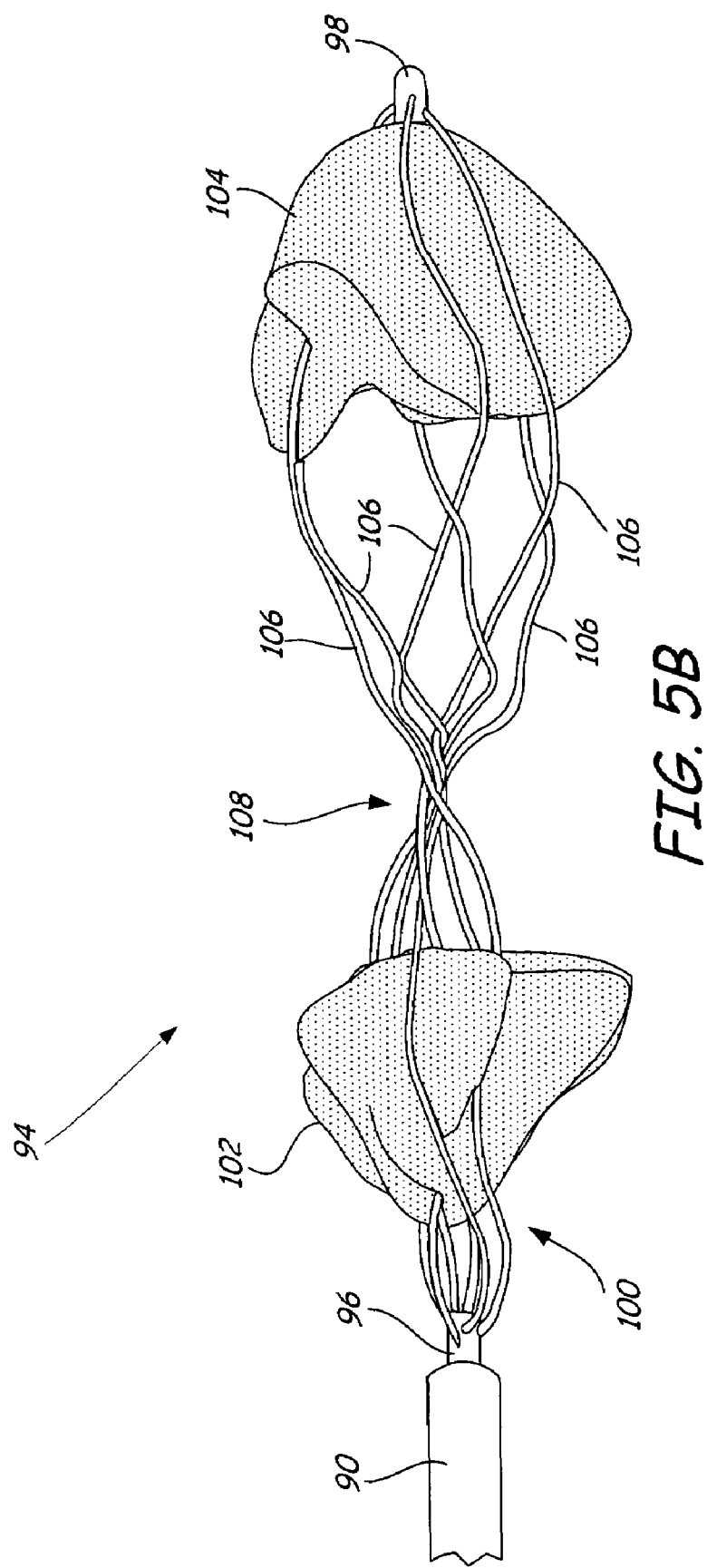

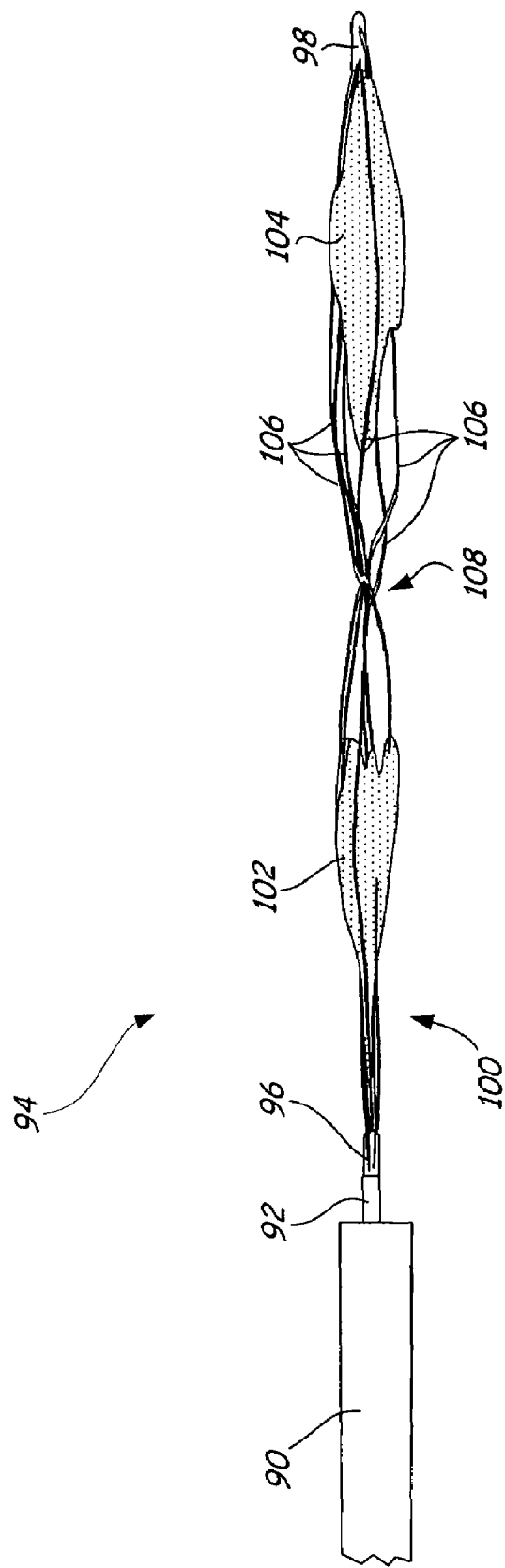

DAISY DESIGN FOR OCCLUSION DEVICE

CROSS-REFERENCE TO RELATED APPLICATION(S)

None.

BACKGROUND OF THE INVENTION

This invention relates to an occlusion device for the closure of physical apertures, such as vascular or septal apertures. More specifically, this invention relates to an occlusion device that self-centers across a defect and can be retrieved and redeployed in situ.

The heart is generally comprised of four chambers: the left and right atrium and the left and right ventricle. Separating the left and right sides of the heart are two walls, or septa. The wall between the two atria is the interatrial septum, and the wall between the two ventricles is the interventricular septum. There are several defects which can affect the septa of both children and adults, including patent ductus arteriosus, patent foramen ovale, atrial septal defects (ASDs), and ventricular septal defects (VSDs). Although the causes and physical characteristics of these defects vary by type, these defects may generally comprise an aperture, flap, or hole in the septum which allows blood to shunt between chambers in the heart where there is no blood flow in a normal, healthy heart. This abnormal blood flow can cause a variety of health problems.

Normally, permanently repairing certain cardiac defects in adults and children requires open heart surgery, which is a risky, painful, and expensive procedure. Surgically closing an aperture in the heart requires the patient to undergo general anesthesia and requires opening of the chest cavity. The patient may spend several days in the hospital and may take several weeks to recover before being able to return to normal levels of activity.

To avoid the risks and discomfort associated with open heart surgery, modern occlusion devices have been developed that are small, implantable devices capable of being delivered to the heart through a catheter. Rather than surgery, a catheter inserted into a major blood vessel, and an occlusion device is moved through the catheter to the treatment site where it can then be deployed at the defect. This procedure is performed in a cardiac cathlab, and avoids the risks, pain, and long recovery associated with open heart surgery.

There are currently several types of occlusion devices capable of being inserted via a catheter including, button devices, collapsible umbrella-like structures, and plug-like devices. These modern occlusion devices can repair a wide range of cardiac defects, including patent foramen ovale, patent ductus arteriosus, atrial septal defects, ventricular septal defects, and may occlude other cardiac and non-cardiac apertures.

One form of occlusion device generally has a first side, a second side, and a center section. Once the occluder is deployed, the first side is positioned on one side of the aperture to be occluded, and the second side sits in the other side of the aperture. The occluder's center section extends through the center of the defect or aperture being occluded. The left and right sides occlude the aperture on the respective sides of the aperture. Because the center section of the occlusion device may be small relative to the size of the aperture to be occluded, it is a challenge to ensure the occlusion device is properly centered across the aperture.

Further, the size of defects varies from patient to patient, with some defects being larger than others. If the defect is large, it is desired that the center section of the occluder remain in the center of the defect so that the first and second sides of the occluder are optimally positioned to occlude the entire defect. If the center section not optimally centered, the first and second sides of the occluder may not be optimally placed so that the defect is properly occluded. If the defect is not properly occluded, blood may continue to shunt through the defect lessening the effectiveness of the occluder.

Many occluders are designed so that the first and second sides are collapsible, allowing the occluder to fit inside a catheter. When in the collapsed position, it is desired that the occluder be highly compact so that the smallest diameter catheter may be used when deploying the occluder. A catheter with a smaller diameter reduces trauma, improves maneuverability, and allows the device to be used in patients who have small vasculature or who are very young. Loading the device into a small diameter catheter must be done by hand, requires a high degree of manual dexterity, and can be time consuming.

Once the device is loaded, it is maneuvered through the catheter to the treatment site within the body, where it is then deployed. In the event the device is not optimally deployed, it may be retrieved, and the procedure may be performed again. While some types of occlusion devices are retrievable via catheter, many require open heart surgery to be retrieved.

Even in instances where the device can be retrieved using a catheter, retrieval may require insertion of a larger diameter catheter than that used for insertion. A larger diameter catheter may be required because the device may not readily resume the compact shape it had before deployment. Once retrieved, the device may be compromised from the stress of withdrawing it back into the catheter, even if a larger diameter catheter has been used. As such, it may not be possible to reuse the retrieved occlusion device.

In addition, devices retrieved via catheter are typically not properly loaded for redeployment. Thus, even if the device is retrievable, the device must be pulled back through the catheter and be completely removed from the catheter so that it can be properly reloaded. Reloading is time consuming, additional time to the procedure, and creates wear and tear on the device. Often, the retrieved device cannot be reused because it has been damaged by the retrieval process. If the device cannot be reused, a new device is required, which increases the cost of the procedure.

Thus, there is a need in the art for an occlusion device that is easily loaded into a catheter, and that can be retrieved, reloaded, and redeployed in situ. There is also a need in the art for an occlusion device which has a centering system to improve the ability of the device to be centered in the defect.

BRIEF SUMMARY OF THE INVENTION

The present invention relates to an occlusion device which can be more easily centered in a defect, and which is capable of being retrieved in situ. The occlusion device comprises a first post configured to be located on a first side of a defect, a second post configured to be located on a second side of the defect, and a fixation device connected to the first and second posts. The fixation device is used to hold the occlusion device in place across a defect, and comprises several segments. The segments are shaped so that each segment comprises a loop, causing the fixation device to resemble a "daisy."

More specifically, proximate to the loop on each segment is a first radial portion extending from the first post to the loop and a second radial portion extending from the loop to the second post. When the device is deployed, the first post and the first radial portions of the segments are located on a first side of the defect. Similarly, the second post and the second radial portions of the segments are located on a second side of the defect. The loop portions of the segments extend through the defect and help to center the occlusion device in defect.

BRIEF DESCRIPTION OF THE DRAWINGS

FIGS. 5A-5C illustrates the occlusion device as it is collapsed to be loaded into a catheter.

DETAILED DESCRIPTION

Figure 1:
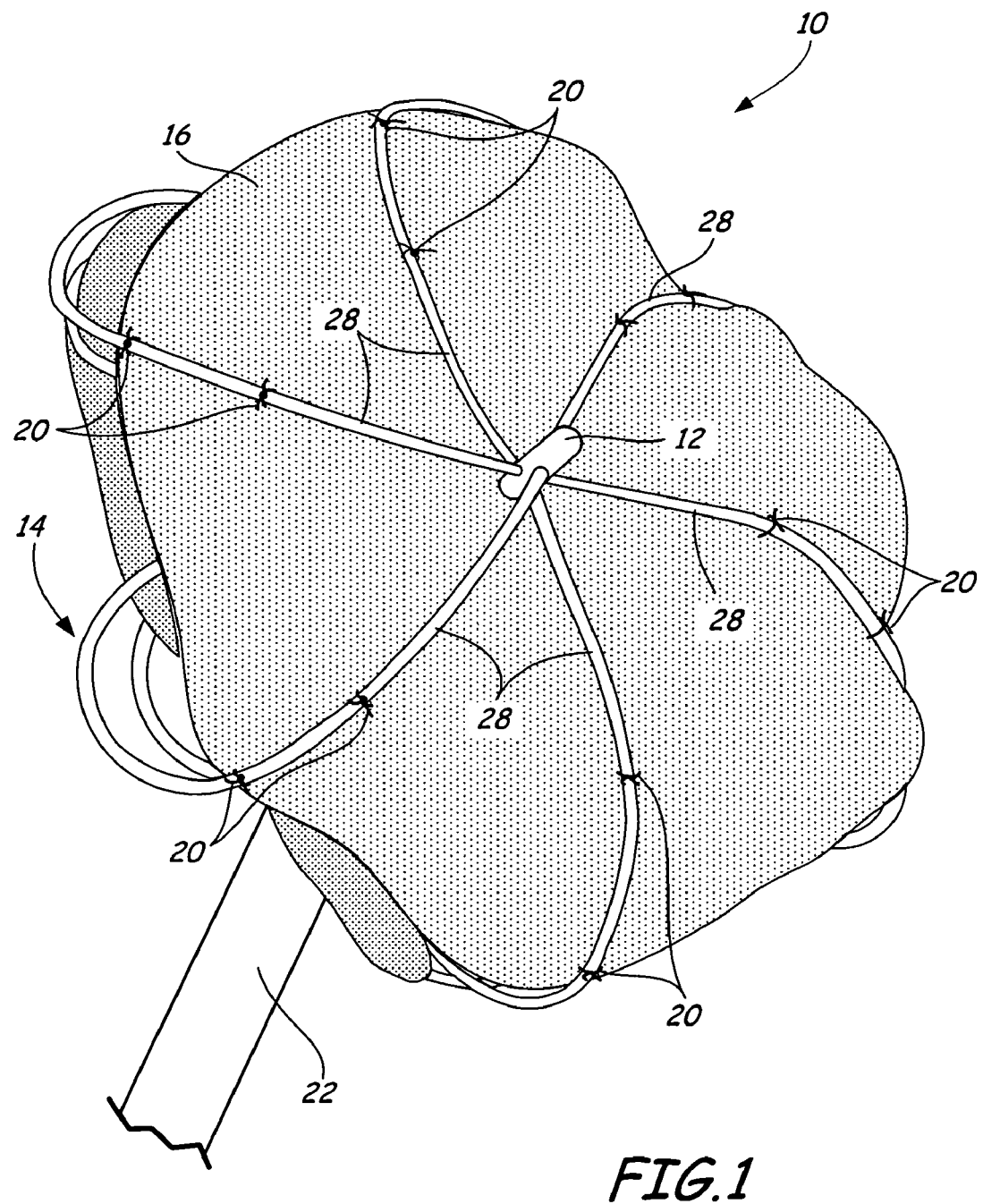
FIG. 1 is a top perspective view of an occlusion device illustrating features of the present invention.

FIG. 1 is a top perspective view of occlusion device 10 suitable for occluding an aperture in the body, such as a cardiac defect. Occlusion device 10 comprises first post or hub 12, fixation device 14, first occluding sheet 16, and second occluding sheet 18. Fixation device 14 is connected to first post 12, and first sheet 16 is attached to fixation device 14. First sheet 16 can be attached to fixation device 14 using any suitable mechanism, such as a plurality of sutures 20. Also visible is catheter 22, which may be used to deploy occlusion device 10.

Figure 2:
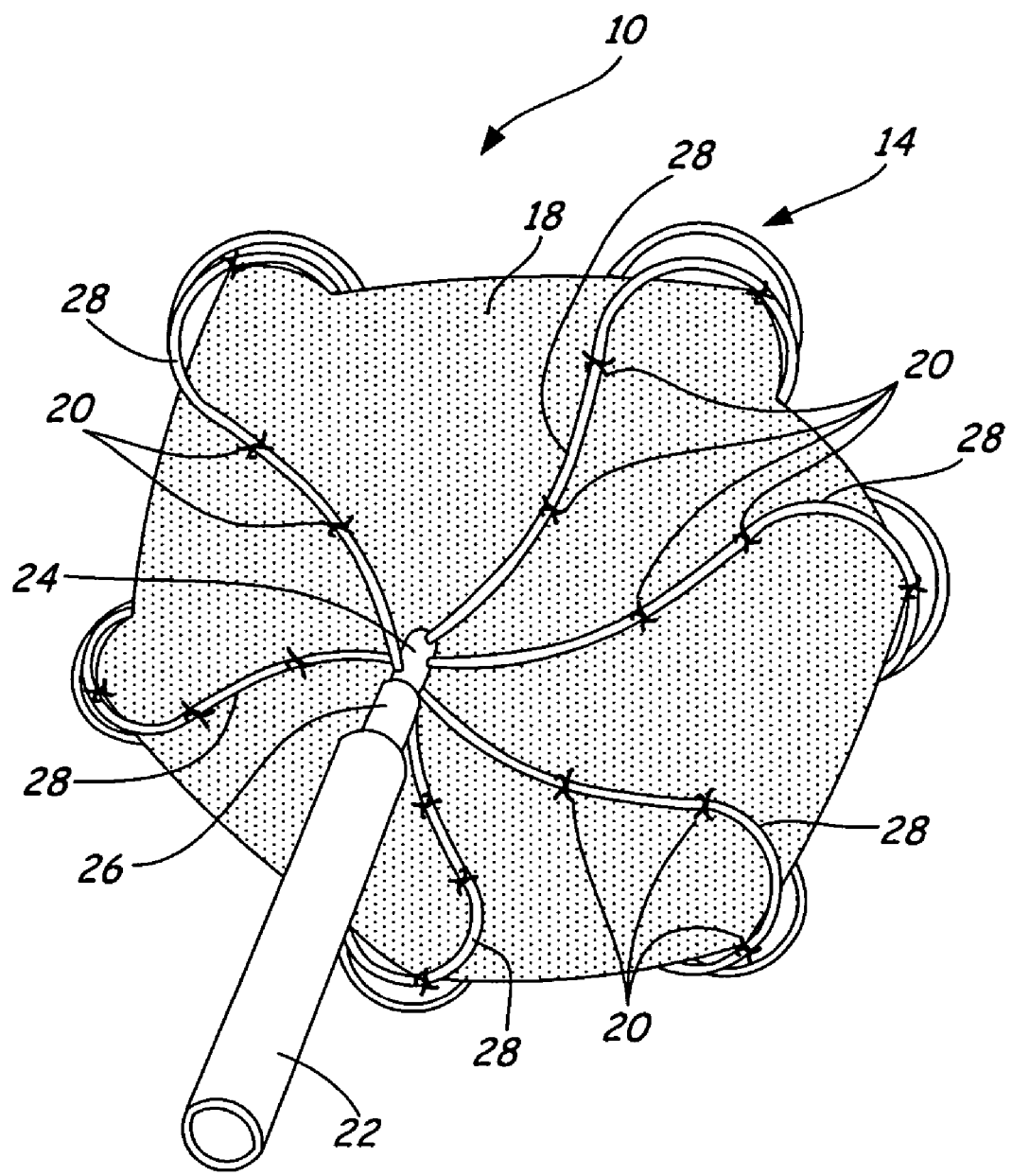
FIG. 2 is a bottom perspective view of an occlusion device illustrating features of the present invention.

FIG. 2 is a bottom perspective view of occlusion device 10. More visible in the bottom perspective view is second sheet 18. Also visible is fixation device 14, second post or hub 24, delivery device 26, and catheter 22. Fixation device 14 also connects to second post 24, similar to the way fixation device 14 connects to first post 12. Also, similar to first sheet 16, second sheet 18 is connected to fixation device 14 using any suitable method, such as sutures 20.

Occlusion device 10 is constructed so that it can be deformed or collapsed and placed into catheter 22. To allow occlusion device 10 to be collapsed for placement into catheter 22, fixation device 14 is designed to be deformable from the starting configuration illustrated in FIGS. 1-2. First and second sheets 16, 18 attached to fixation device 14 are also flexible, and are configured to fold as fixation device 14 is collapsed. The manner in which occlusion device 10 can be collapsed so that it can be deployed through catheter 22 is described in greater detail below with reference to FIGS. 5A-6B.

Occlusion device 10 is connected to delivery device 26, preferably at second post 24. Delivery device 26 connects to occlusion device 10 in any suitable manner, such as by a threaded connection or using any suitable form of forceps. Delivery device 26 is used to hold occlusion device 10, such as when occlusion device 10 is being loaded into catheter 22, occlusion device 10 is being moved through catheter 22, or when occlusion device 10 is being deployed at a defect.

When occlusion device 10 is deployed, sheets 16, 18 are positioned on opposing sides of the defect and serve to occlude the defect. Fixation device 14 is used to hold occlusion device 10 in place, and to urge sheets 16, 18 against the tissue adjacent the defect being occluded. Sheets 16, 18 are preferably connected to occlusion device 10 so that sheets 16, 18 are located on the inside of fixation device 14. However, occlusion device 10 is not so limited, and sheets 16, 18 may be attached at any location as desired or suitable.

Sheets 16, 18 may be any suitable material, and preferably are comprised of a medical grade polymer in the form of film, foam, gel, or a combination thereof. One suitable material is a high density polyvinyl alcohol (PVA) foam, such as that offered under the trademark IVALON®. To minimize the chance of occlusion device 10 causing a blood clot, foam sheets 16, 18 may be treated with a thrombosis inhibiting material. One such suitable material is heparin.

To ensure there is sufficient tension to hold sheets 16, 18 in place, fixation device 14 is made of a suitable material, such as metal wire. More preferably, fixation device 14 is formed of a material capable of shape memory. One suitable material is a nickel-titanium alloy, commonly called Nitinol. Nitinol is preferably used because it is commercially available, very elastic, non-corrosive and has a fatigue life greater than that of stainless steel. Fixation device 14 may also be heat treated to increase shape memory. To further ensure that fixation device 14 is sufficiently durable and does not suffer from fatigue failure, one embodiment of the present invention comprises making fixation device 14 of stranded wire or cables.

Fixation device 14 comprises six individual portions, or arms 28. However, occlusion device 10 is not so limited. Occlusion device 10 may comprise any suitable number of arms 28. Further, the exact shape of fixation device 14 can be varied based on the desired characteristics of fixation device 14, such as the amount of tension required to hold occlusion device 10 in place across the defect, or the ability of occlusion device 10 to self center in a defect. As such, occlusion device 10 may be formed of fewer arms 28, such as four, or more arms 28, such as eight, or ten as long as fixation device 14 is capable of maintaining the position of occlusion device 10.

Preferably, fixation device 14 is designed with arms 28 arranged symmetrically about center post 12, 24 so that the angles between each adjacent arm 28 are about equal. Placing fixation device 14 symmetrically about center post 12, 24 is preferable because it ensures that fixation device 14 more evenly applies pressure against the tissue proximate occlusion device 10 when it is in place. When formed of six arms 28, each arm 28 may be separated from adjacent arm 28 by approximately 60 degrees. However, the invention is not so limited, and arms 28 may be arranged at any angles desired or suitable.

Figure 3:
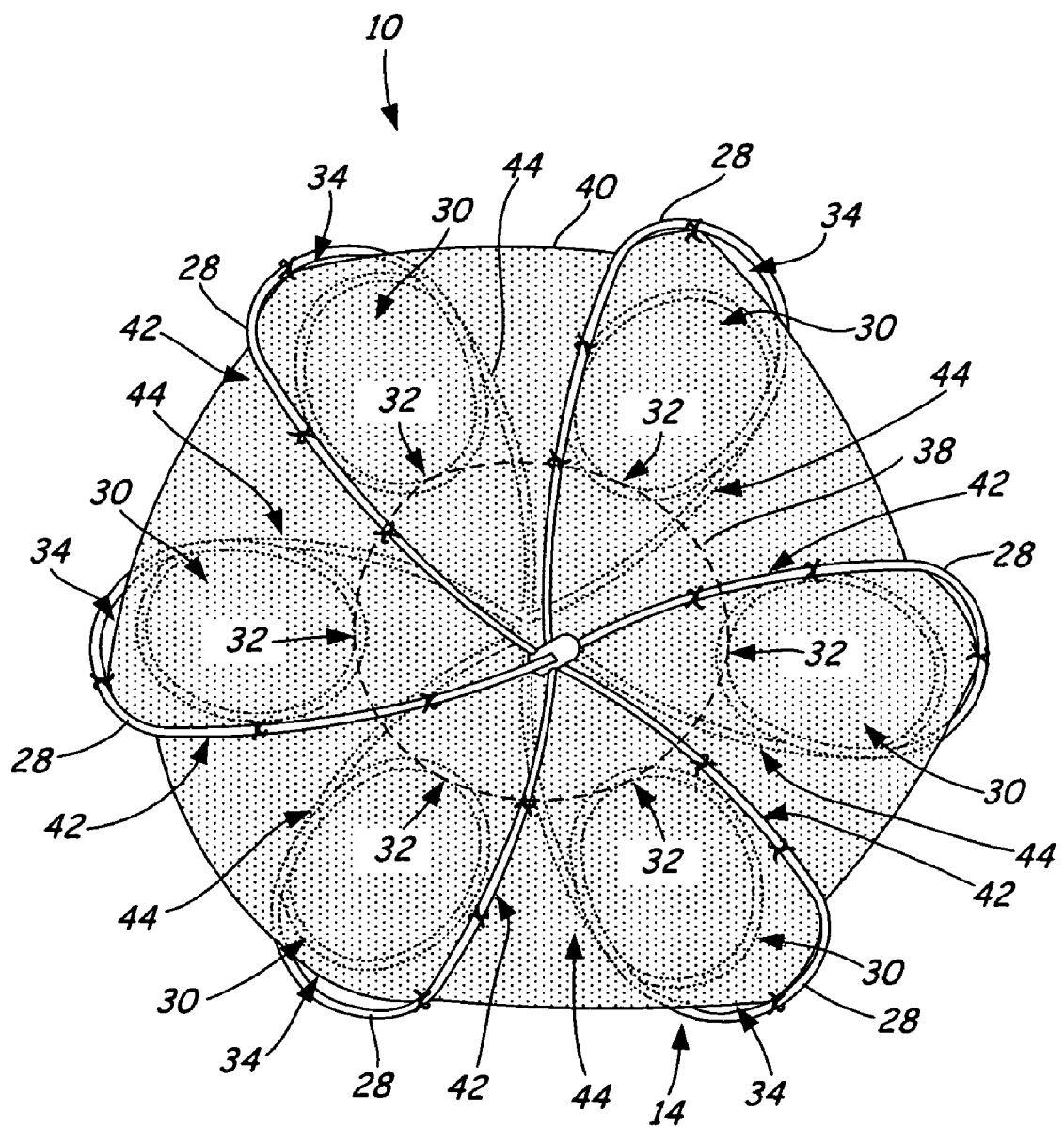
FIG. 3 is a top plan view of the occlusion device.

FIG. 3 is a top plan view of occlusion device 10 more clearly illustrating the design of fixation device 14. As can be seen in FIG. 3, each arm 28 of wire fixation device 14 is shaped so that it comprises a loop 30. Because of the shape of arms 28, the loops 30 resemble a flower shape having several petals, or a "daisy design." Relative to center post 12, each loop 30 has a proximal side 32 and a distal side 34. An effective inner diameter 38, indicated by dashed line 38, is formed by proximal sides 32 of each loop 30. Similarly, distal sides 34 of loops 30 correspond to outer diameter 40 of occlusion device 10. Each arm 28 is essentially a one-turn spring, and comprises loop 30, first radial portion 42, and second radial portion 44. When inserted in a defect, first radial portion 42 is designed to be placed on one side of the defect and second radial portion 44 is placed on the opposite side of the defect. Between first radial portion 42 and second radial portion 44 is loop 30. When deployed, loop 30 extends through the defect and helps to center occlusion device 10 in the defect. Previous devices typically utilized two occluding bodies connected by a center post, with the center post extending through the defect. Such devices are difficult to center in the defect because the center post often has a diameter much smaller than the size of the defect. Thus, when placed across a defect, the center post has minimal ability to center the device in the defect. Instead, the device must be carefully deployed to ensure it is centered.

In contrast, occlusion device 10 is designed to be self centering. The self centering feature is due to occlusion device 10 having a much larger effective center created by inner diameter 38. One or more of proximal sides 32 of loops 30 may contact the tissue at the perimeter of the defect. In doing so, loops 30 help arrange occlusion device 10 in the defect so that it is more effectively centered.

Inner diameter 38 and outer diameter 40 can be used to accurately select the size of occlusion device 10 which best fits the defect to be occluded. More specifically, when selecting the appropriate occlusion device 10 to occlude a defect, a decision can be made as to the appropriate size of occlusion device 10 by correlating effective inner diameter 38 created by proximal sides 32 of loops 30, or effective outer diameter 40 created by distal sides 34 of loops 30, or possibly both, to the size of the defect.

Figure 4:
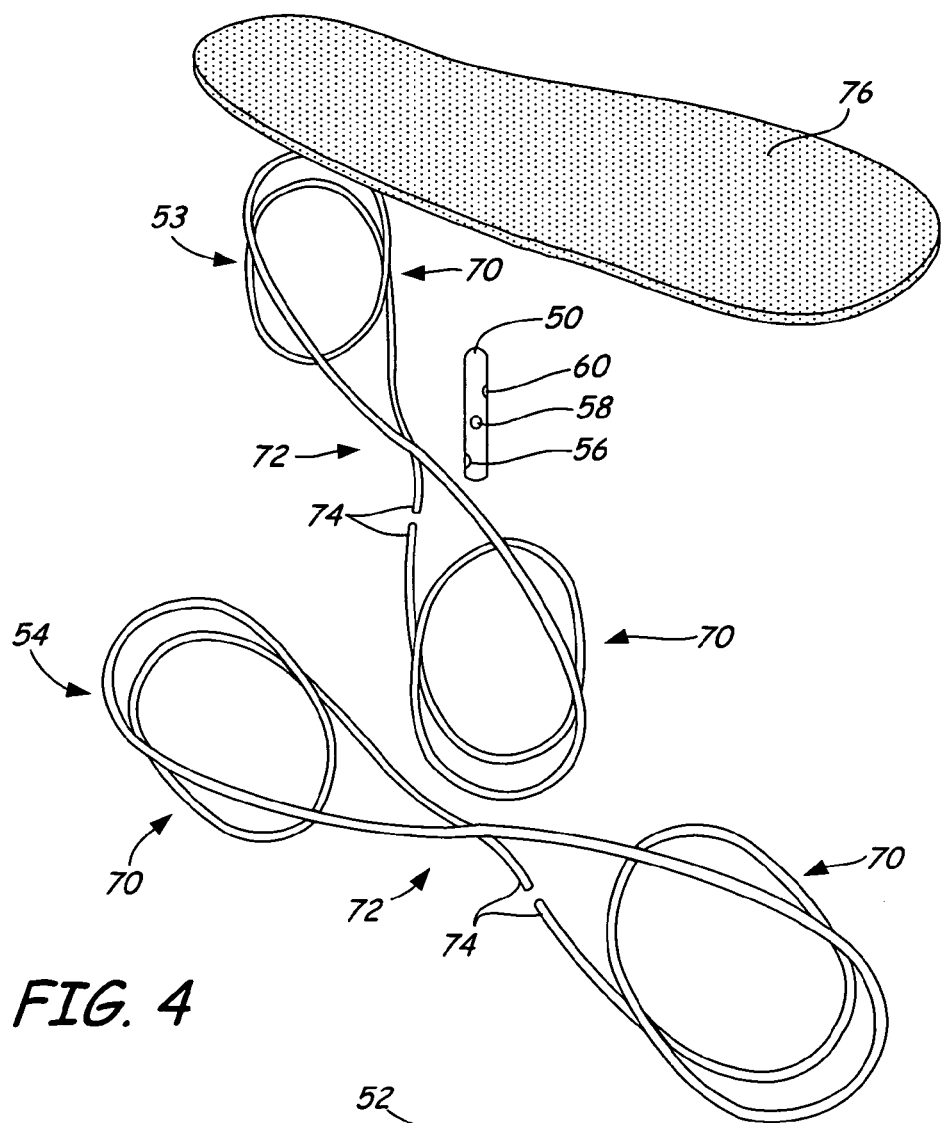
FIG. 4 is an exploded perspective view of the fixation device of the occlusion device.
Figure 4:
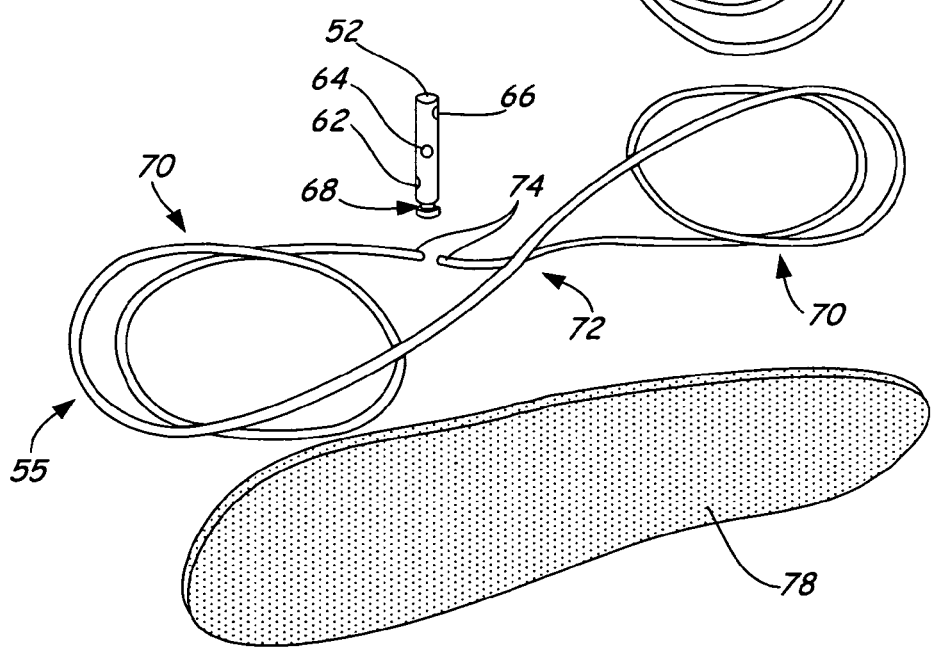

FIG. 4 is an exploded view of an occlusion device illustrating one manner of forming occlusion device 10. Shown in FIG. 4 is first center post 50, second center post 52, and three fixation members 53, 54, 55. First post 50 comprises first hole 56, second hole 58, and third hole 60. Similarly, second post 52 comprises first hole 62, second hole 64, and third hole 66. Second post 52 further comprises knob 68 located at one end.

In the embodiment illustrated in FIG. 4, each wire fixation member 53, 54, 55, comprises two loop portions 70. Between two portions 70 is center section 72. Because each of fixation members 52, 53, 54, are formed of a single wire, the two ends 74 of the wire meet at center section 72. Also shown are two sheets 76, 78, which are attached to fixation members 52, 53, 54 in any suitable manner, as described above.

One method of assembling fixation device 14 is to connect each fixation member 53, 54, 55, to first and second center post 50, 52 at the holes 56-66. One suitable way to do so is to thread first fixation member 53 through top hole 60 of first post 50 until center section 72 of fixation member 53 is located about at hole 60. Similarly, second fixation member 54 is inserted into second hole 58 so that center section 72 of fixation member 54 is located at hole 58 in first center post 50. Finally, third fixation member 55 is inserted into third hole 56 of first center post 50 so that first center post 50 is located near center section 72 of third fixation member 55.

Similarly, ends 74 of first fixation member 53 are connected to second post 50 at third hole 66. Likewise, ends 74 of second fixation member 54 are connected to second center post 52 at second hole 64, and ends 74 of third fixation member 55 are connected at third hole 62.

When connecting members 53, 54, 55 to first and second center posts 50, 52, any suitable method may be used. For instance, members 53, 54, 55 may be welded, crimped, adhered, or otherwise connected to center posts 50, 52. Alternately, fixation members 53, 54, 55 may simply be inserted holes 56-66 on first and second posts 50, 52. Further, although each fixation member 53, 54, 55 is shown as formed from a single wire, the invention is not so limited. Each arm may be formed of a separate length of wire, and may be connected to center posts 50, 52 in any suitable manner.

To ensure that each fixation member is arranged so that it is radially separated from an adjacent fixation member by approximately 60 degrees, holes 56-66, may be formed in center posts 50, 52 at various angles to each other. Further, to ensure the post 50, 52, retain the strength required, yet remains small, holes 56-66 may be arranged vertically along the posts 50, 52 so that when the holes are drilled, center posts 50, 52 remain structurally sound. The arrangement of holes 56-66 on center posts 50, 52 further ensures that when the occlusion device is collapsed for insertion into a catheter, any overlapping of wire fixation members 53, 54, 55 is minimized. Minimizing the overlapping of fixation members 53, 54, 55, particularly near center posts 50, 52, helps decrease the overall bulk of the occlusion device, and allows for the use of small diameter catheters.

Figure 5A:
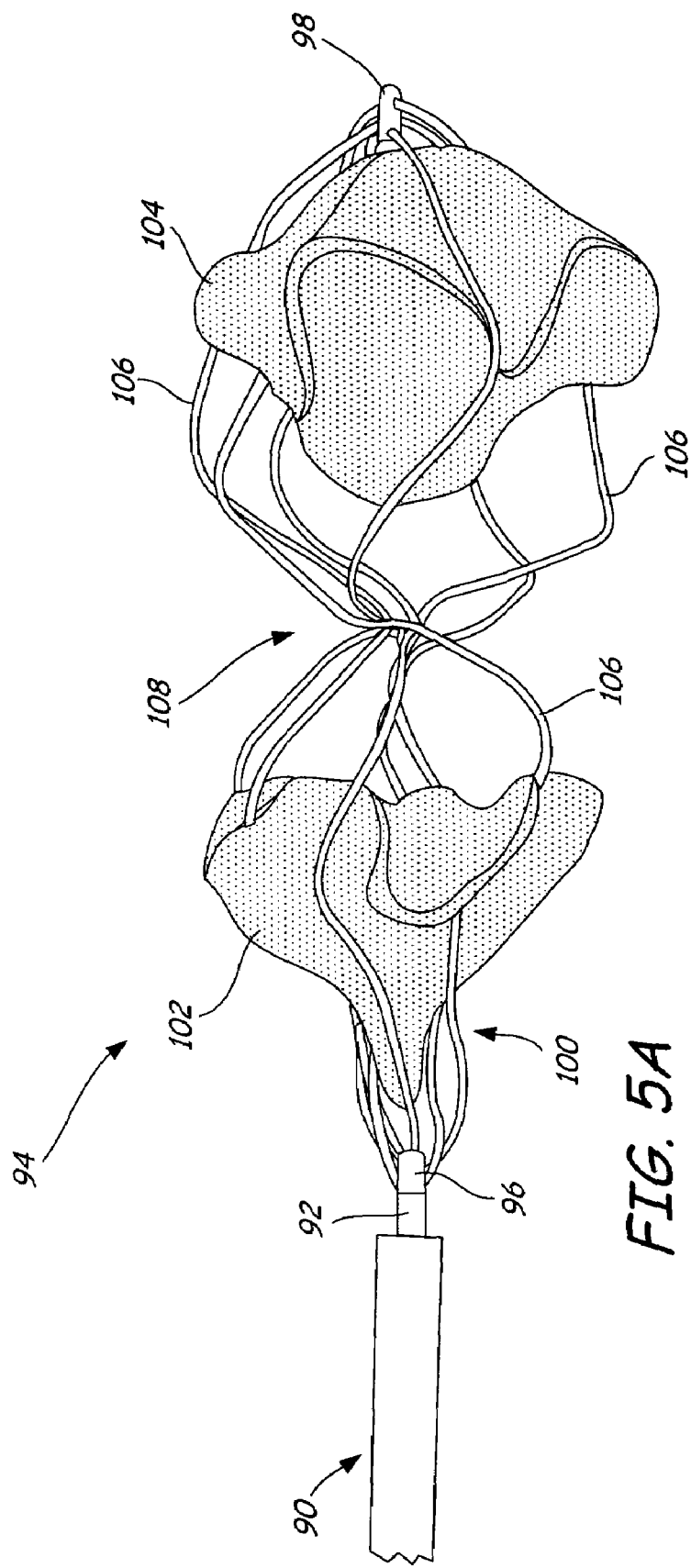

FIGS. 5A-5C illustrate one advantage of the occlusion device of the present invention. In deploying an occlusion device, it is preferred that the occlusion device be collapsible to fit within a small diameter catheter, with the smallest diameter catheter possible being preferred. Furthermore, it is desired that the occlusion device be easily loaded into the catheter. Finally, once an occlusion device has been deployed in a defect, it is desired that the occlusion device be easily retrievable should it be placed at a less than optimal location across the defect. Due to the design of the fixation device, the present invention is easily loaded into small diameter catheters and is also easily retrievable in situ.

Shown in FIG. 5A, is catheter 90, grasping device 92, and occlusion device 94. Occlusion device 94 comprises first center post 96, and center second post 98. As described above, connected between first and second center posts 96, 98 is fixation device 100. Attached to fixation device 100 is first sheet 102 and second sheet 104. Fixation device 100 corresponds to the daisy design described above, and is formed of individual fixation segments 106 which, in their undeformed states, comprise a loop between two radial portions, as illustrated and described above.

As viewed in FIG. 5A, fixation device 100 comprises middle section 108 located between first and second sheets 102, 104. Middle section 108 corresponds to the location of loop portions (illustrated above with reference to FIGS. 1-4) of fixation device 100.

To allow occlusion device 94 to be inserted into catheter 90, occlusion device 94 must be collapsed or folded. To do so, first center post 96 is pulled away from second post 98. Upon doing so, fixation device 100 begins to deform, with individual fixation segments 106 beginning to straighten. More specifically, as illustrated in FIG. 5A, as first center post 96 is pulled apart from second center post 98, each loop of fixation segments 106 begins to uncoil. At the same time, first and second sheets 102, 104 begin to fold.

FIG. 5B illustrates occlusion device 94 as first center post 96 continues to be pulled away from second center post 98. Middle section 108 of fixation device 100 further uncoils, and fixation members 106 straighten even more. Similarly, first and second sheets 102, 104 become more folded as fixation members 106 contact sheets 102, 104 and as fixation members 106 uncoil and straighten.

In one embodiment, sheets 102, 104 are attached to wire fixation device 100 so that as wire fixation device 100 collapses, sheets 102, 104 remain on the inside of fixation device 100. This increases the durability of occlusion device 94 as it is loaded into catheter 90. More specifically, as occlusion device 94 is withdrawn into catheter 90, fixation device 100 is the first part of occlusion device 94 to contact edges of catheter 90 as it is loaded. Because fixation device 100 is preferably formed of wire, it is more robust than sheets 102, 104. Ensuring that it is wire fixation device 100 which contacts the catheter first minimizes potential damage to sheets 102, 104. This design also reduces the chance that sheets 102, 104 may become separated from fixation device 100 or damaged by catheter 90 as they are pulled into it.

As can be seen in FIG. 5B, it is possible to ensure that second sheet 104 is connected to second post 98, as well as connected to wire fixation device 100. However, occlusion device 94 is not so limited. Alternately, as illustrated with first sheet 102, it is not necessary to suture sheet 102 to center post 96. However, suturing either sheet 102, 104 to center post 96, 98 may be desirable because the suturing helps to hold sheets 102, 104 in place as desired during loading and unloading and after occlusion device 94 has been deployed across a defect.

FIG. 5C provides an illustration of occlusion device 94 once it has been collapsed for insertion into catheter 90. Given the design of fixation device 100, when fully collapsed, occlusion device 94 is capable of fitting into a very small diameter catheter 90. Because the loops of fixation members 106 are fully uncoiled, the bulk created by wire fixation device 100 is greatly minimized when in the collapsed position. Further, as described above, placement of fixation members 106 along center posts 96, 98, as well as how fixation members 106 are connected to center posts 96, 98, further serves to reduce the bulk of occlusion device 94 when it is in the collapsed position.

More specifically, staggering the placement of fixation members 106 along the length of center posts 96,98 serves to prevent all of fixation members 106 folding at one location along center posts 96,98. Similarly, varying the angles at which fixation members 106 are inserted into center posts 96,98 further serves to reduce the bulk of occlusion device 94 when fixation members 106 fold at center posts 96, 98 areas. The bulkiest portion of fixation device 100 becomes the area where first and second sheets 102, 104 are folded. As a result, the size of catheter 90 can be greatly reduced.

In previous devices, the occlusion device may comprise several wire arms emanating from a center post. The ends of the wire arms were often capped with atraumatic tips to minimize damage to tissue contacted by the wire arms. When inserting such an occlusion device into a catheter and the arms were folded in the axial direction along the center post, the tips often overlapped. This caused increased bulk on the device at the location of the atraumatic tips when the device was folded for insertion into a catheter. As a result of this increased bulk, a larger catheter was required. In contrast, the present invention does not require the use of atraumatic tips at the ends of the arms, and thus does not experience the same challenges in ensuring the tips do not form a cluster when the arms are folded. As a result, the device is less bulky and can be used with a smaller diameter catheter.

Another challenge for previous occlusion devices formed of several wire arms emanating from a center post related to the high degree of manual dexterity required for loading the devices into the catheter. For instance, to insert such an occlusion device into a catheter, a first set of wire arms must be folded in one direction, while at the same time a second set of arms is folded in the opposite direction. Loading the occlusion device into a catheter while ensuring the arms are properly folded in the correct directions often proves difficult.

In contrast, the present invention is readily inserted into a catheter. The device can be grasped at the end posts using any suitable method, such as by using a delivery device to grasp one end post and a user's fingertips to grasp the other end post. By simply pulling the two grasped posts away from each other, the device is readily collapsed for easy loading into the catheter.

Not only is the ability of loading the new occlusion device into a catheter improved, but also the design of the fixation device of the present invention makes the device easily retrievable. Should a user feel that one or both sides of the occlusion device are not optimally seated at the defect, either side of the occlusion device can be easily retrieved by simply pulling it back into the catheter, and forcing the device to collapse as described above with reference to FIGS. 5A-5C.

Another advantage of the present invention is that once retrieved, due to the manner in which the fixation device collapses the device, the occlusion device is properly loaded in the catheter, and thus is readily available for redeployment in situ. Once again, both sides have this unique feature. Thus, if it is necessary to reposition either side, or the entire device, both sides are easily retrievable, and once retrieved, are properly loaded for another attempt at deployment.

Other previous occlusion devices are formed of a wire mesh material. The large amount of metal required to form the device has certain disadvantages. For instance, the metal structure may eventually suffer fatigue and break, requiring removal or replacement of the device. The present invention achieves the ability to fit into a small diameter catheter while still minimizing the amount of metal wires needed to form the fixation device.

Figure 6A:
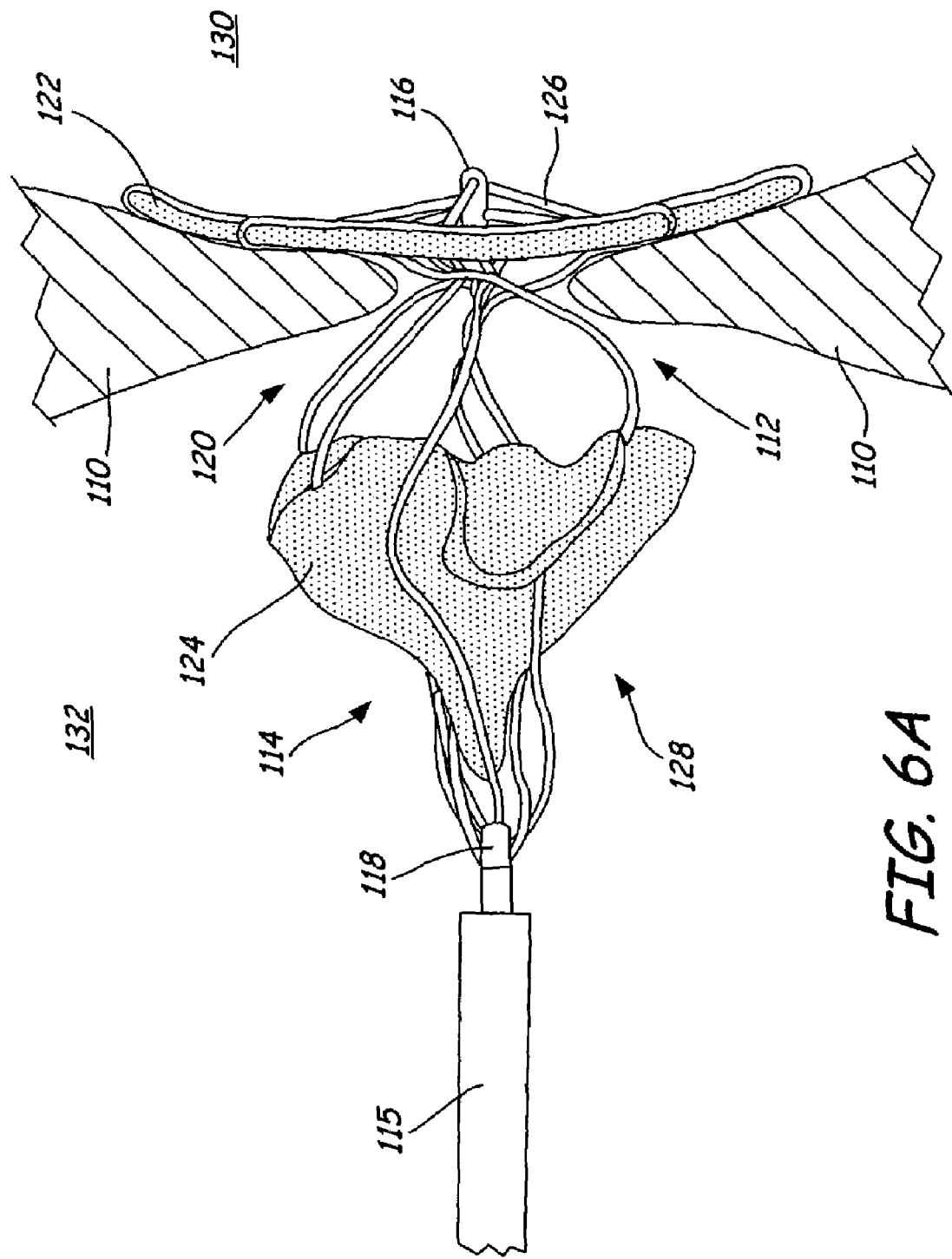
FIGS. 6A-6B are side perspective views of the occlusion device implanted in a septal aperture.
Figure 6B:
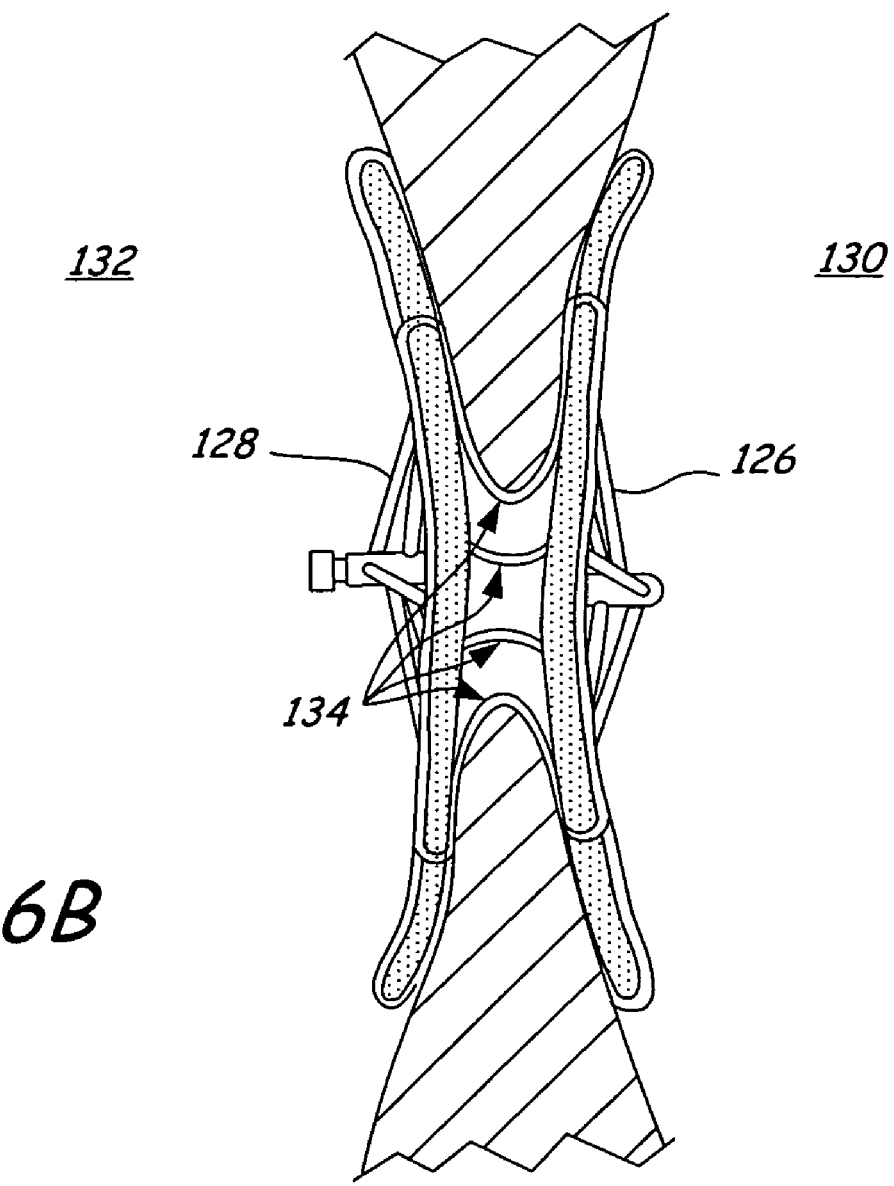

FIGS. 6A and 6B illustrate an occlusion device as it is deployed across a defect. Shown in FIG. 6A is a portion of septal wall 110 having septal aperture 112. Occlusion device 114 is shown being deployed across septal aperture 112. Similar to the occlusion devices described above, occlusion device 114 comprises catheter 115, first center post 116, second center post 118, fixation device 120, first sheet 122, and second sheet 124. Fixation device 120 comprises first arm portions 126 on a first side 130 of a defect, and second arm portions 128 on a second side 132 of a defect.

To insert the occlusion device 114 across septal aperature 112, catheter 115 is positioned proximate defect 112. Occlusion device 114 is advanced through catheter 115 until a first arm portions 126 of occlusion device 114 exits catheter 115. Once the first side of occlusion device 114 has exited catheter 115, fixation device 120 partially returns to its original shape. In returning to its original shape, first arm portions 126 of fixation device 120 partially return to their looped configuration. The radial portions of first arm portions 126 urge first sheet 122 against septal wall 110. In this way, septal aperture 112 is blocked on the first side of septal wall 110.

Next, second arm portions 128 are allowed to exit catheter 115 on second side 132 of septal aperature 112. As shown in FIG. 6A, once allowed to exit catheter 115, the second side of occlusion device 114 begins to return to its original shape. To do so, second arm portions 128 of fixation device 120 begin to return to their original shape, and in doing so, begin to unfold second sheet 124.

As shown in FIG. 6B, both sides 126, 128 of occlusion device 114 have been deployed. Catheter 115 has been withdrawn, along with the grasping device used to hold second center post 118. Once fixation device 120 has returned to its original shape memory configuration, fixation device 120 is arranged so that the first radial portions of first arm portions 126 are located on first side 130 of septal aperature 112, and the second radial portions of second arm portions 128 are located on second side 132 of septal aperature 112. Arm portions 126, 128 hold first and second sheets 122, 124 against septal wall 110.

Loop portions 134 are formed as part of first and second arm portions 126, 128. Loop portions 134 of fixation device 120 are arranged across septal aperature 112. Because loop portions 134 of fixation device 120 pass through septal aperature 112, loop portions 134 may contact portions of the tissue surrounding the septal aperature 112. This contact helps to center occlusion device 114 in septal aperature 112.

Although the present invention has been described with reference to preferred embodiments, workers skilled in the art will recognize that changes may be made in form and detail without departing from the spirit and scope of the invention.

The invention claimed is:

1. A device for use in occluding an aperture, the device comprising:
   a first post;
   a second post;
   a plurality of arms, each arm comprising a first radial section extending outward from the first post, a second radial section extending outward from the second post and a loop comprising a greater than 360 degree helical turn connecting the first and second radial sections; and
   first and second sheets attached to each arm, each sheet having an inside face and an outside face, the inside faces facing inwardly toward one another, and the outside faces of the first and second sheets facing outwardly away from one another and toward the first and second posts, respectively,
   wherein the first sheet is positioned along an inside length of each first radial section and the second sheet is positioned along an inside length of each second radial section such that each first and second radial section extends radially along and contacts at least a portion of the outside face before extending over an outer peripheral edge of the first and second sheets, respectively, and the loops extend between the inside faces of first and second sheets, each loop having a radial innermost portion that passes through and engages an edge of the aperture so that the loops create a flexible inner diameter capable of self-centering the device with respect to the aperture.

2. The device of claim 1 wherein each arm is a wire formed of nickel titanium.

3. The device of claim 1 wherein each arm is formed to have shape memory.

4. The device of claim 1 wherein each arm is formed of stranded wire.

5. The device of claim 1 wherein the device comprises six arms.

6. The device of claim 1, wherein the loop comprises an approximately 540 degree turn.

7. The device of claim 1, wherein the first and second posts are cylindrical hubs.

8. An occlusion device for closing an aperture, the occlusion device comprising:
   a first post;
   a second post;
   a fixation device comprising a plurality of fixation segments, wherein each fixation segment comprises:
      a first radial portion connected to the first post,
      a second radial portion connected to the second post, and
      a loop comprising an approximately 540 helical degree turn extending between the first and second radial portions; and
   first and second occluding sheets each having an inside face and an outside face, the inside faces facing inwardly toward one another, and the outside faces of the first and second occluding sheets facing outwardly away from one another and toward the first and second posts, respectively, the occluding sheets positioned inside the fixation device such that the first and second radial portions of each fixation segment extend radially along and contact at least a portion of the outside face before extending over an outer peripheral edge of the first and second occluding sheets, respectively, and the loops extend between the inside faces of first and second occluding sheets, each loop having a radial innermost portion that passes through and engages an edge of the aperture so that the loops create a flexible inner diameter capable of self-centering the device with respect to the aperture.

9. The occlusion device of claim 8 wherein the first post further comprises a grasping knob.

10. The occlusion device of claim 8 wherein the first sheet is connected to the fixation device using sutures at the first radial portions of the fixation segments.

11. The occlusion device of claim 8 wherein the first sheet is connected to the fixation device using sutures at the first radial portions of the fixation segments and the second sheet is connected to the fixation device using sutures at the second radial portions of the fixation segments.

12. The occlusion device of claim 8 wherein the plurality of fixation segments comprises six arms.

13. The occlusion device of claim 8 wherein the plurality of fixation segments are formed of stranded wire.

14. The occlusion device of claim 13 wherein each fixation segment has a shape memory.

15. The occlusion device of claim 13 wherein the plurality of fixation segments are formed of nickel titanium.

16. The occlusion device of claim 8 wherein the plurality of fixation segments are connected to the first post so that each fixation segment is about 60 degrees from an adjacent fixation segment.

17. The occlusion device of claim 8 wherein the plurality of fixation segments comprises three wires.

18. The occlusion device of claim 8 wherein the first and second posts have holes therein, and the fixation segments are connected to the first and second posts at the holes.

19. The occlusion device of claim 18 wherein the holes comprise three holes arranged vertically along each of the first and second posts.

20. An occlusion device, the occlusion device comprising:
   a first post;
   a second post;
   a collapsible support frame connected between the first and second posts, wherein the support frame comprises a plurality of wire segments, each wire segment including a coil comprising an approximately 540 degree helical turn, each coil having a radial innermost portion for passing through and engaging an edge of a defect so that the coils create a flexible inner diameter capable of self-centering the device with respect to the defect; and
   first and second occluding sheets each sheet having an inside face and an outside face, the inside faces facing inwardly toward one another, and the outside faces of the first and second occluding sheets facing outwardly away from one another and toward the first and second posts, respectively, the occluding sheets disposed within the collapsible support frame such that each wire segment emanates from the first post, extends radially along and contacts at least a portion of the first outside face, extends over an outer peripheral edge of the first occluding sheet, forms the coil between the inside faces of first and second occluding sheets, extends over an outer periphery of the second occluding sheet, extends radially along and contacts at least a portion of the second outside face, and terminates at the second center post.

21. The occlusion device of claim 20 wherein the wire segments are formed of a material having shape memory.

22. The occlusion device of claim 20 wherein the wire segments are formed of stranded wire.

23. The occlusion device of claim 20 wherein the wire segments are arranged so that each wire segment is about 60 degrees from an adjacent wire segment.

24. The occlusion device of claim 20 wherein the wire segments are formed of three wires.

25. The occlusion device of claim 24 wherein the collapsible support frame is connected to the first and second posts so that the three wires are arranged vertically along each of the first and second posts.

26. The occlusion device of claim 20 wherein the first occlusion sheet and the second occlusion sheet are connected to the collapsible frame using sutures.

* * * * *